United States Patent [19]

Johnson et al.

[11] Patent Number: 5,047,719
[45] Date of Patent: Sep. 10, 1991

[54] FLEXIBLE COIL ASSEMBLY FOR REFLECTANCE-MODE NONDESTRUCTIVE EDDY-CURRENT EXAMINATION

[75] Inventors: Duane Johnson, San Mateo; Yehuda Krampfner, Pleasanton, both of Calif.

[73] Assignee: The Failure Group, Inc., Menlo Park, Calif.

[21] Appl. No.: 528,753

[22] Filed: May 25, 1990

[51] Int. Cl.⁵ .................... G01N 27/82; G01R 33/12; H01F 21/02
[52] U.S. Cl. .................................. 324/242; 324/262; 336/20
[58] Field of Search ................ 324/234, 236, 239–243, 324/262, 263; 336/20, 200

[56] References Cited

U.S. PATENT DOCUMENTS

| | | |
|---|---|---|
| 4,139,822 | 2/1979 | Urich et al. |
| 4,467,281 | 8/1984 | Davis et al. |
| 4,495,587 | 1/1985 | Plante et al. |
| 4,543,528 | 9/1985 | Baraona |
| 4,593,245 | 6/1986 | Viertl et al. |
| 4,639,708 | 1/1987 | Weatherly |
| 4,706,020 | 10/1987 | Viertl et al. |
| 4,706,021 | 11/1967 | Chameul .............................. 324/242 |
| 4,719,422 | 1/1988 | de Walle et al. |
| 4,733,023 | 3/1988 | Tamaru et al. |
| 4,740,753 | 4/1988 | Glover et al. |
| 4,755,753 | 7/1988 | Chern |
| 4,757,258 | 7/1980 | Kelly et al. |
| 4,763,274 | 8/1989 | Junker et al. |
| 4,918,418 | 4/1990 | Tsala .................................. 336/200 |

OTHER PUBLICATIONS

Krampfner et al, "Flexible Eddy Current Coil Arrays", Fossil Plant Inspections Workshop (1986).

*Primary Examiner*—Walter E. Snow
*Attorney, Agent, or Firm*—Thomas P. Liniak

[57] ABSTRACT

An improved flexible coil array for nondestructive reflective-mode eddy-current testing of conductive members is disclosed. The assembly comprises a flexible substrate having a first array of coils formed on one side thereof. The first array of coils are connected in series in parallel columns. One end of each of the rows is connected to a common ground connection, while the other ends of each row are successively connected to a source of excitation energy. A second array of series-connected rows of coils, orthogonal to the columns, is formed on the opposite side of the substrate. Again, one end of each of the rows is connected to a common point while the other end of each of the rows is successively connected to means for detecting a voltage induced on the coils of the row. The voltage will vary if one of the coils is disposed in juxtaposition to a discontinuity of the member to be inspected. Comparison of voltages induced on the various rows of coils, together with indication of the column of driver coils which is being driven at the time of detection of a variation in the voltage, locates any discontinuity in the member to be inspected. The coils may be made up of pairs of half-coils connected in series to form the rows and columns.

26 Claims, 6 Drawing Sheets

FLEXIBLE COIL ASSEMBLY FOR REFLECTANCE-MODE NONDESTRUCTIVE EDDY-CURRENT EXAMINATION

FIELD OF THE INVENTION

This invention relates to an improved flexible coil assembly for reflectance-mode nondestructive eddy-current examination. More particularly, this invention relates to a system, method, and flexible coil assembly for nondestructive eddy-current examination of conductive members which may be curved or contoured.

BACKGROUND OF THE INVENTION

The prior art has sought for many years to provide useful systems and methods for nondestructive examination and testing of critical parts such as aircraft and automotive structural members, machine elements, architectural members, turbine blades, and the like. A wide variety of nondestructive examination methods have been developed. One of the more useful of these is eddy-current testing. Broadly stated, this method involves placement of an inductor, typically a coil of wire, into close physical juxtaposition to an electrically conductive member to be tested and energizing the coil with a sinusoid, typically at a frequency between a few Hz and 100 MHz. The magnetic field from the coil penetrates the mass of the member to some extent and induces an eddy current therein. By monitoring the response of the coil to the applied signal, an evaluation of the impedance of the overall system can be derived. If the coil is then moved a short distance with respect to the part to be inspected and the process repeated, a similar value can be detected. Eventually, the entire member can be thus examined. Discontinuities in the sequence of detected values which do not correspond to discontinuities intended by the designer of the part suggest that the part is flawed, i.e., includes a crack, a void, or the like.

The prior art shows a number of patents directed at coil structures for this and related uses. Flexible coils have been the subject of many patents and other publications, inasmuch as many such parts are not simple planar members. See, for example, Viertl et al U.S. Pat. Nos. 4,593,245 and 4,706,020 and Weatherly U.S. Pat. No. 4,639,708.

Conventionally, such coils are connected as part of a balancing circuit, such as a Wheatstone bridge circuit, which provides a very accurate and simple method for measuring a change in impedance of the coil. That is, the circuit is balanced or "nulled", after which any departure from the null position of the circuit can readily be measured. For example, in U.S. Pat. No. 4,107,605 to Hudgell, one or two sets of four coils, each of spiral shape, are connected in a bridge circuit and are provided on a flat or profiled substrate to conform to the surface of the member under test.

A balancing circuit for multiple-coil eddy-current probes is shown in U.S. Pat. No. 4,651,093 to Detriche et al. Other patents generally discussing eddy-current testing of workpieces include Baraona U.S. Pat. Nos. 4,543,528 and 3,886,793 to Cramer et al. Other circuits for use with eddy-current distance measuring detectors and the like are shown in Kawabata et al U.S. Pat. Nos. 4,288,747 and 4,042,876 to Visioli, Jr.

It is also an object of the art to form coils in a simple manner, desirably by printing conductors on a substrate, as opposed to winding wires on a bobbin or the like. See, for example, U.S. Pat. No. 4,301,821 to Frances, which shows spiral inductors printed on either side of a flexible substrate and connected by way of a through-hole at the center. Frances does not appear particularly to discuss the application of this coil to eddy-current examination of conductive members.

It will be appreciated from the above that using a single-coil inductor to generate an eddy current in a workpiece for inspection purposes necessitates that the probe be physically scanned over the member to be examined. Obviously, it would be desirable to avoid this complexity. The Detriche patent discussed above shows a probe consisting of an array of discrete coils separately addressed by individual leads connected to a multiplexing unit to reduce the number of movements required. However, the resolution of this system, that is, its ability to provide an "image" of a flaw to be detected in a part, is limited by the number of coils in the probe assembly, which in turn is limited simply by the number of wires which can be conveniently connected between the probe and the multiplexer.

To address this limitation, the inventors and others have attempted to develop arrays of coils on a flexible substrate organized into rows and columns so as to be individually addressable, and so that the impedance signals detected by each coil can be compared to one another to locate defects in a part under the array. For example, in FIG. 2, there is shown a 60-element test probe 10 which was developed by the assignee of the application as part of a system described in "Flexible Substrate Eddy-Current Coil Arrays", a paper published in 1986 by one of the present inventors.

Figure 2:
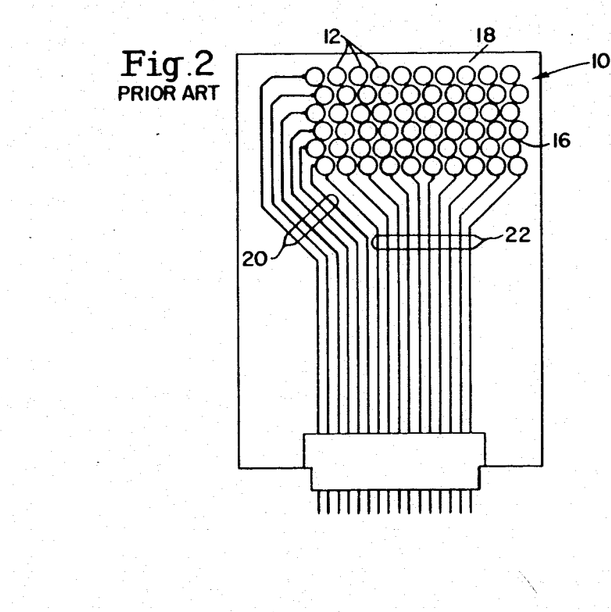
FIG. 2 shows a planar view of the prior art coil array of the system of FIG. 1.
Figure 3:
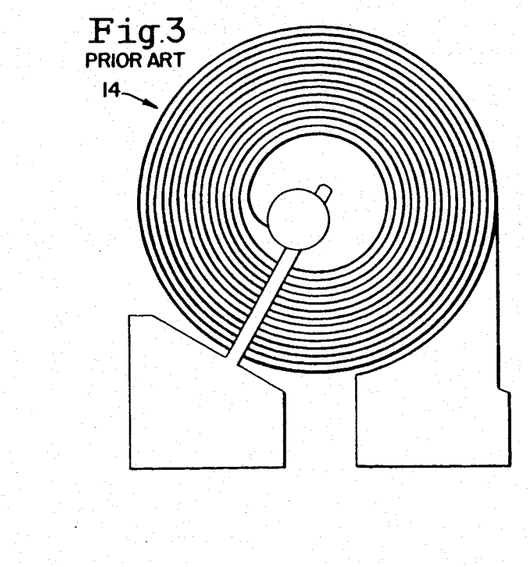
FIG. 3 shows an enlarged view of one of the coils 14 of the prior art array.
Figure 4:
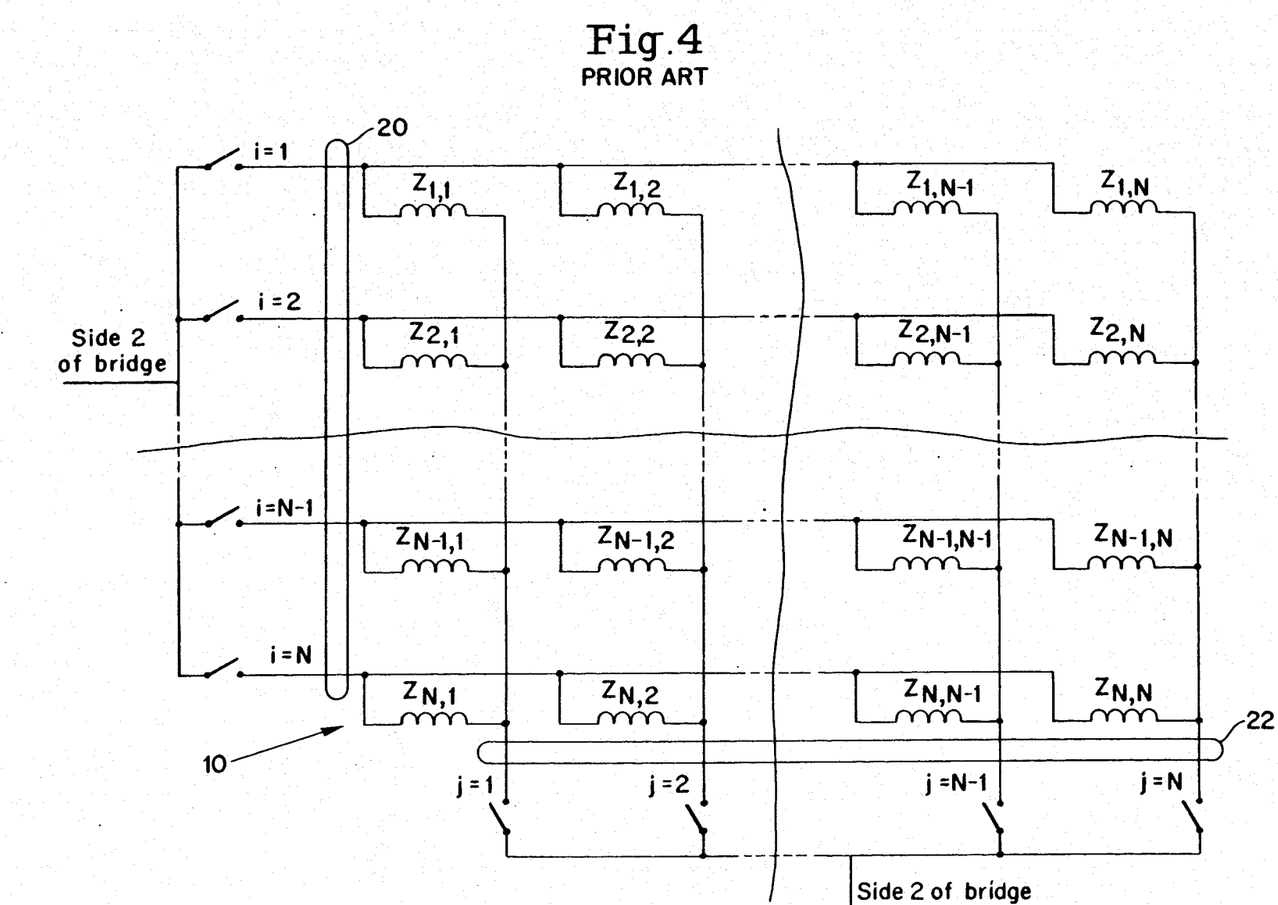
FIG. 4 shows the effective circuit of the prior art coil array.

The prior art probe 10 consists of an array of six rows of coils 12, each row consisting of ten individual coils 12, each of which is generally as depicted in FIG. 3. The circuit of the probe 10 is shown in FIG. 4. One terminal of each of the coils 12 in each of the six rows is connected in common to a row addressing switch, and the second terminal of each of the coils 12 of each column is connected to a column addressing switch. When it is desired to examine a member underneath the substrate 18 on which the coils and the conductors interconnecting the coils are formed, a signal is applied between the appropriate one of the row leads indicated at 20 and the corresponding one of the column leads indicated generally at 22. Because the coils 12 in the rows and columns are effectively connected in parallel, there is substantial "leakage", such that the exciting signal does not drive only the particular coil of interest, but also all of the other coils on the array, to an extent which depends on the resistance of the individual coils and the number of coils.

More specifically, for the 60-element array of FIG. 2, it is found that the particular coil connected directly receives approximately 25% of the energy, while the remaining 75% is spread out among the other coils in the array, with none of them receiving more than on the order of 6% of the total energy. As the coil directly addressed receives four times as much energy as any of the other coils, the variation of its impedance signal is sufficiently stronger than that of any of the other coils so that the effective signal-to-noise ratio is not uselessly low.

However, if the number of elements in the array is increased, the difference between the amount of energy driving the coil at the junction between the row and column to which power is applied and that driving the other coils is reduced substantially. This limits the number of elements which can be usefully provided in an array as shown in FIGS. 2-4. As it is desired that the elements be closely spaced to provide resolution of correspondingly small defects in the part to be examined, the array of FIG. 2 is only capable of examining relatively small portions of members. Therefore, this device does not solve the problem of requiring physical scanning of the probe over the part to be inspected.

Of course, it would be possible to provide separate connections to each of the coils of the array, as in the Detriche patent discussed above. This would allow individual addressing of each coil. However, this would require an individual connection to each of the coils, which would lead to a prohibitively large number of connecting wires. For example, in the array of FIG. 2 having n rows and m columns, n+m conductors and a ground connection are required. If each coil of the array were to be separately connected, this would require $(n \times m) + 1$ conductors—an amount of conductors which would be very awkward to handle, even for a relatively small array such as shown in FIG. 2.

Most prior eddy-current inspection systems, including that of FIG. 2, have operated, as explained above, in the "impedance-mode", wherein the inductor used to induce an eddy current in the part to be inspected is also used to detect the response of the part; that is, the free-space impedance of the driver coil is effectively known, and changes in its impedance which occur when it is juxtaposed to a particular part to be inspected are measured. Sudden variations in the impedance are indicative of discontinuities in the part.

An alternative to impedance-mode eddy-current testing referred to as "reflectance-mode" eddy-current testing can also be performed, wherein a first conductor carries a current which induces an eddy current in the member, and a different conductor is used to measure the corresponding induced voltage. Again, the electromagnetic properties of successive portions of the part are successively measured, so that variations in these properties not corresponding to desired discontinuities in the part indicate flaws. More specifically, the art shows multi-conductor reflectance-mode arrays for sequentially examining portions of a member to be inspected without physically scanning the sensor over the part. Individual elements of an array of driver elements are successively driven with a suitable signal, and the induced voltages detected using an array of detector elements are compared to locate flaws.

For example, Chamuel U.S. Pat. No. 4,706,021 discloses a "crossed wire defect detector employing eddy currents". This consists, in a particularly pertinent embodiment shown in FIG. 2, of a first series of parallel wires 18 extending in a first direction and arranged to be successively connected to a source of energy 26 by a multiplexing switch 27. The other ends of the wires are connected together and grounded as shown. An orthogonally-arranged second array of parallel wires 24 is closely juxtaposed to but electrically insulated from the first set of wires. A first end of the second series of wires 24 is connected together and grounded, as shown, while a second multiplexing switch 29 is used to successively connect the wires 24 to processing electronics 31, which effectively compares the signals induced on the individual wires 24. A sudden change in the signal detected from one wire to the next can indicate the presence of a flaw 28 in a member 22 to be inspected.

One of the difficulties with the Chamuel approach is its inherent poor sensitivity to small defects. In order to complete the drive and pick-up circuits, the ground connectors shown must return to the processing electronics. The wires thus behave effectively as relatively large coils, that is, on the order of the overall array size. It is well known that the sensitivity of a coil to small defects varies indirectly with the coil size.

A second problem with this approach is the large and variable coupling between the drive lines and the pick-up lines. It will be appreciated by those of skill in the art, referring to FIG. 2, that the inductive coupling between the drive circuit and pick-up circuit depends directly upon the physical overlap between the drive circuit and the pick-up circuit. The voltage induced on the pick-up circuit when the drive voltage is connected to the upper line will be much larger when the processing circuit is connected to the left-most line than when processing circuit is connected to the right-most line. These "intrinsic" signal variations are much larger than those produced by small defects.

A third difficulty with the Chamuel approach is that, if a defect such as a crack or scratch extends in a direction parallel to the longitudinal extension of the driver wires 24, the defect may fail to be located. To this end, Chamuel proposes, with respect to FIG. 7, using two sets of detector wires orthogonal to one another to insure that no defect can be parallel to both. This only partially solves the problem. It would obviously be desired to eliminate this sensitivity to crack orientation.

It would also be desired to produce other improvements on the Chamuel system, specifically including simplified methods of manufacture, improved signal-to-noise ratio, and provision of reflectance-mode eddy-current testing in a flexible array, which can conform to contoured parts.

Another disclosure generally relevant to eddy-current techniques is U.S. Pat. No. 4,733,023 to Tomaru et al which shows two orthogonal sets of parallel wires under a plate which are successively interrogated to locate the presence of a magnetic member on the surface of the plate. This is not an eddy-current inspection device per se.

SUMMARY OF THE INVENTION

The present invention achieves the needs of the art and objects of the invention described above by its provision of a flexible array for nondestructive eddy-current examination of conductive parts, which comprises a flexible substrate, a first array of series-connected coils arranged in parallel rows on one side of the substrate, and a second array of series-connected coils arranged in parallel columns orthogonal to the rows on the other side of the substrate. The columns of coils are successively provided with a sinusoid of excitation energy, while the induced voltage in each row is successively measured. Discontinuities in the measured voltages are correlated with the location of the pertinent row and column, to locate discontinuities in the material being tested.

In a preferred embodiment, the assembly consists of a driver array consisting of pairs of half coils arranged in columns and a detector array consisting of pairs of half coils arranged in rows. The half coils of the columns are connected in series, as are the half coils of the rows, so that stray inductance associated with the return circuit is essentially eliminated. As each pair of half coils collectively behaves as a continuous circular coil, the arrays are equally sensitive to cracks in any orientation.

A switch for successively directing the excitation energy to the various columns, and a corresponding switch for connecting the various rows to a detector circuit are provided. In the preferred embodiment, a multiplexer is provided to switch the excitation energy and amplify and switch the output signal. A computer based eddy-current instrument is used to control the multiplexer and process and display the test results. Depending upon the application, the multiplexer may be local to the array or local to the test instrument.

BRIEF DESCRIPTION OF THE DRAWINGS

The invention will be better understood if reference is made to the accompanying drawings, in which.

DETAILED DESCRIPTION OF THE PREFERRED EMBODIMENTS

Figure 1:
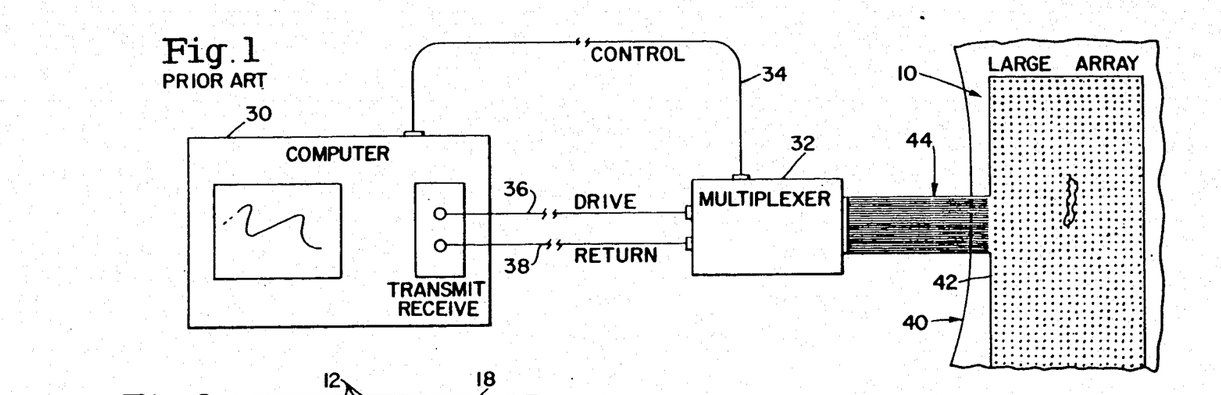
FIG. 1 shows the overall system previously publicly described by the assignee of the applicant and which, therefore, forms part of the prior art, as noted.
Figure 6:
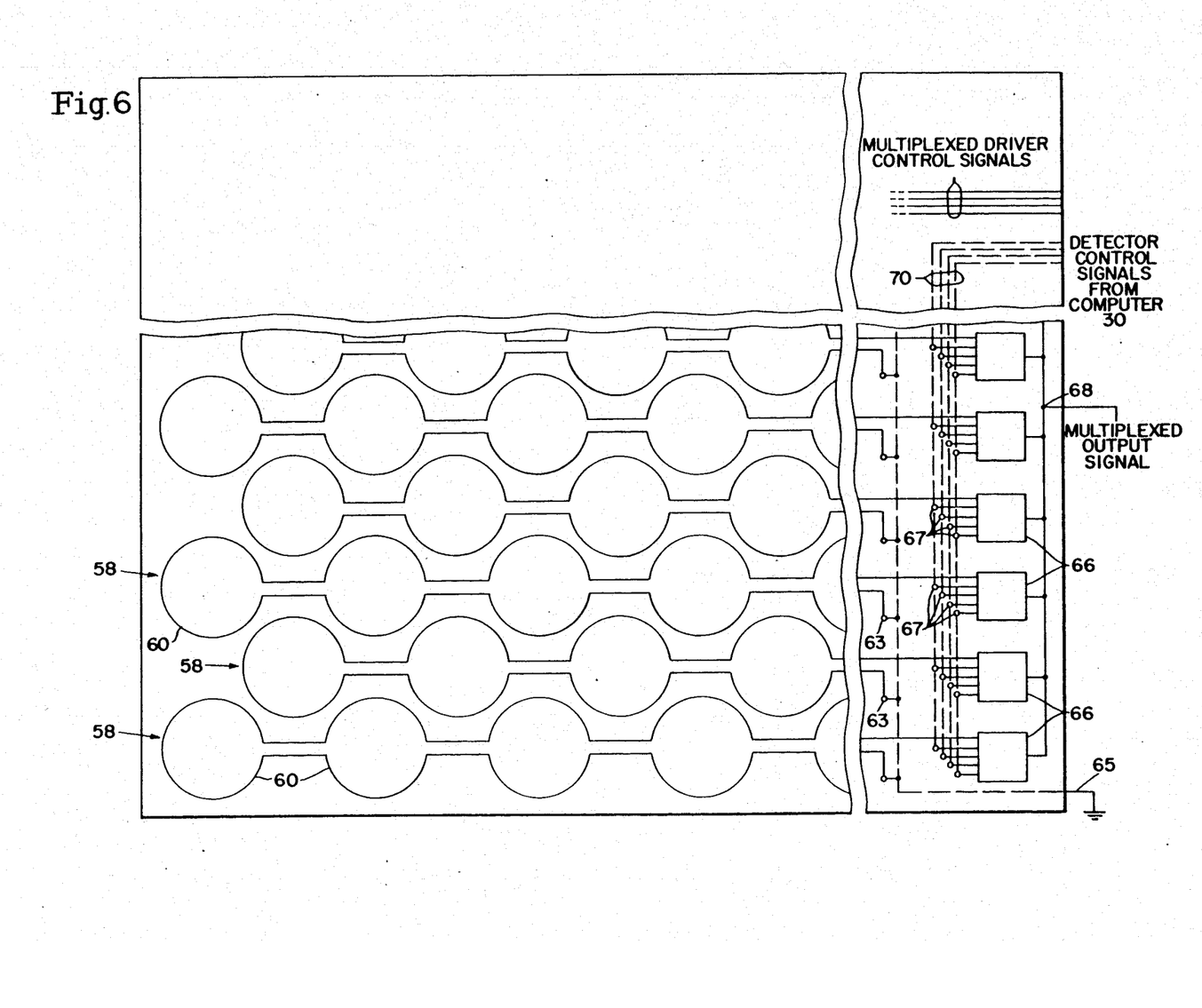
FIG. 6 shows a schematic view of the detector side of the array according to the invention.
Figure 7:
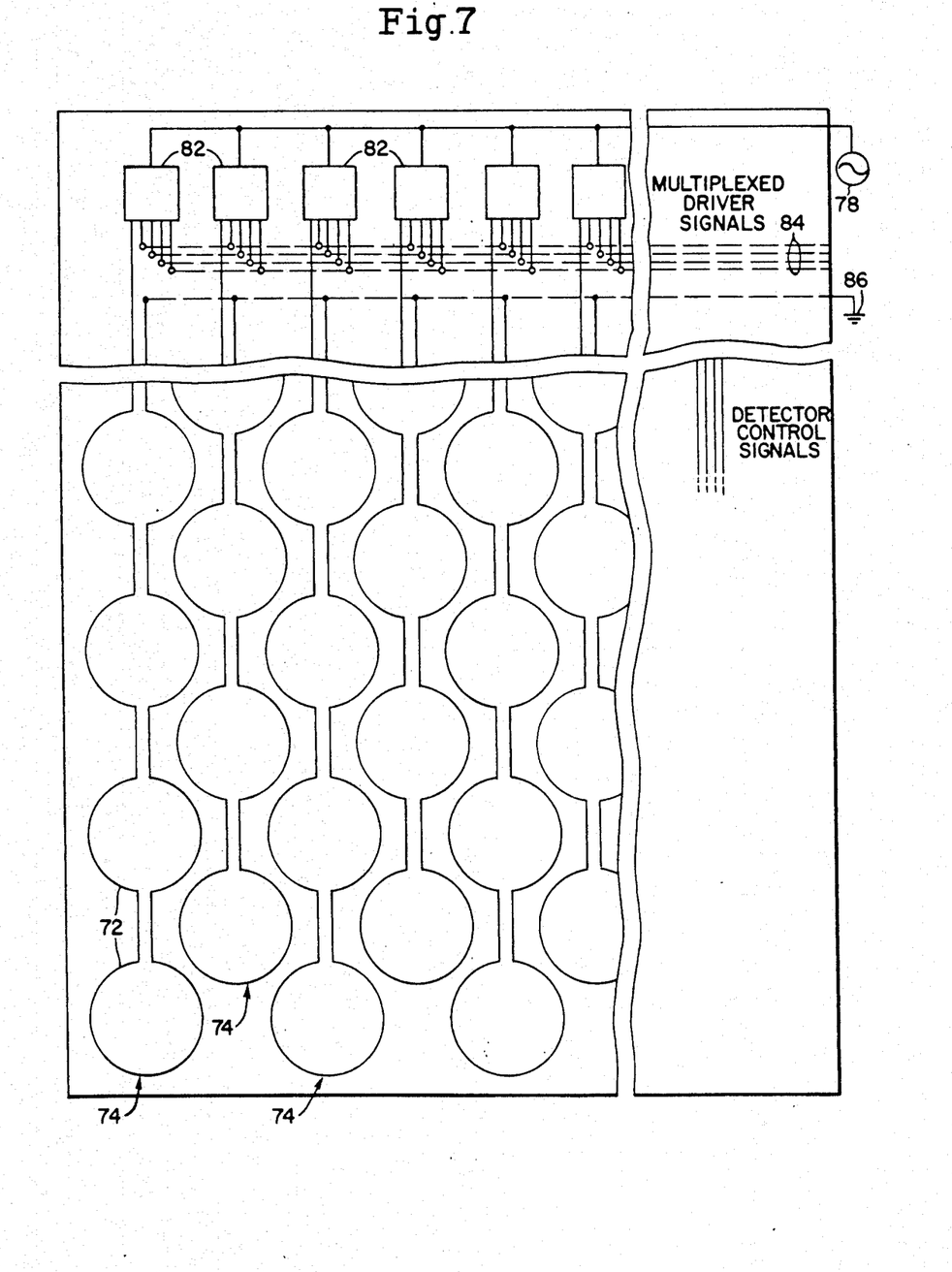
FIG. 7 shows a corresponding view of the driver side of the array according to the invention.
Figure 8:
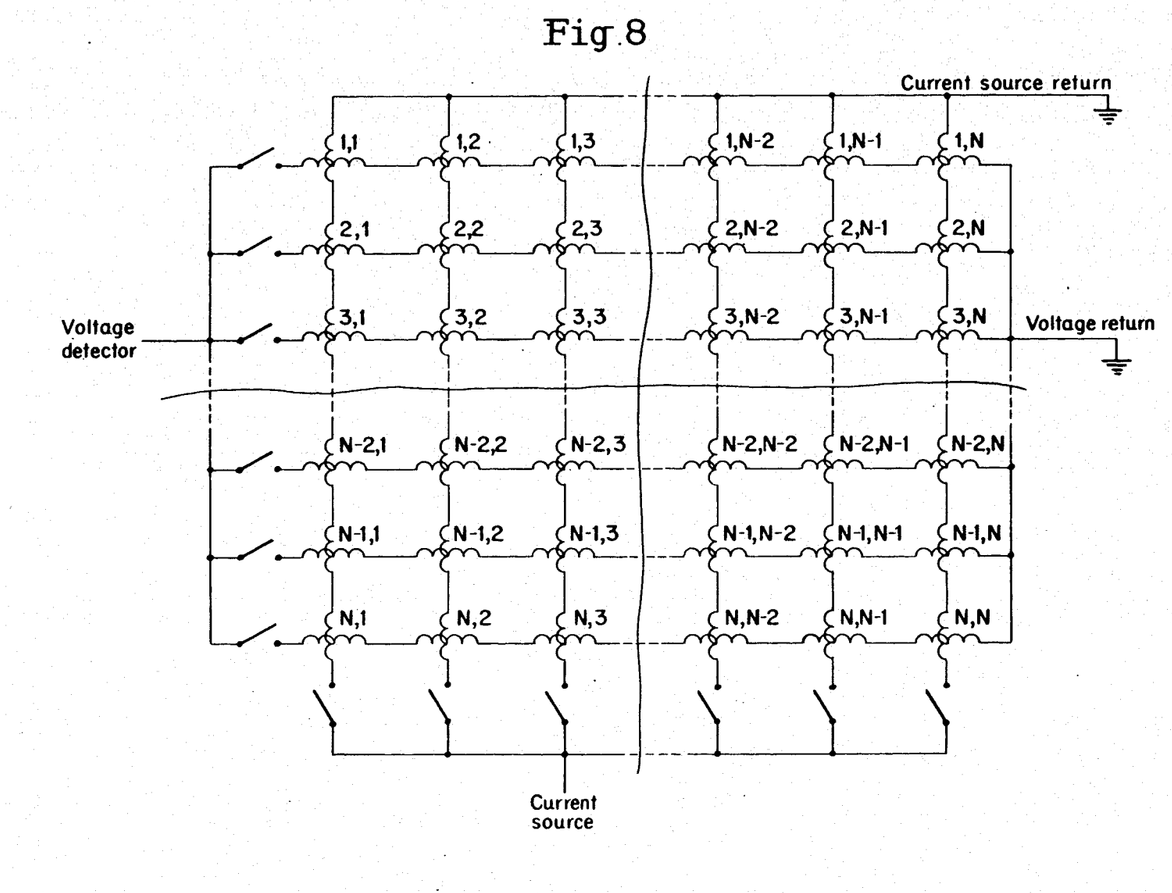
FIG. 8 shows the effective circuit of the coil array according to the present invention.

FIG. 1 shows the overall inspection system of the prior art. According to the present invention, the coil array shown in detail in FIGS. 6-8 is substituted for the array 10 shown in FIG. 1. Apart from minor modifications apparent to those of skill in the art, the other elements of this system are carried over without substantial modification according to the present invention. In this system, a computer-based eddy-current instrument 30 is connected by a number of wires to a multiplexer unit 32. The multiplexer unit 32 comprises a number of internal switches, closed in response to control signals received over a control line 34 from the computer 30, to connect the eddy-current instrument to selected ones of the rows and columns of the detector array of FIG. 2. If the device operates by repetitive measurement of impedance, the eddy-current instrument array may comprise a Wheatstone bridge measuring circuit as described above. Other eddy-current devices are known, as also described above. The multiplexer is also connected to the computer by a drive line 36, which carries the driving signal, typically a simple sinusoid, and a line 38 which carries the return signal. The return signal, indicative of an electromagnetic property of the part, is correlated by the computer 30 with the relative position of the row and column in the array being driven, for example, to locate a discontinuity 42 in a part 40 to be inspected.

As discussed above, FIG. 2 shows an array of coils which are connected to their neighbors in both row and column dimensions, as used in the prior art, for eddy-current inspection of conductive members. FIG. 3 shows an enlarged view of one of the coils. FIG. 4 shows the effective circuit of the array. As indicated, each of the coils is connected between a row line switch i and a column line switch j. To excite the material beneath coil $z_{2,2}$, for example, switch $i=2$ and switch $j=2$ would both be closed. However, it can be observed that alternate current paths between these switches exist, for example, through coils $z_{2,1}$, $z_{1,1}$ and $z_{1,2}$, as well as many other combinations. While most of the energy will flow through coil $z_{2,2}$, as all alternate current paths involve additional impedance, the energy is substantially dissipated by the alternate current paths. Therefore, it was not possible using this circuit to only excite one of the coils of the system, or to only excite all of the coils of one of the rows, or similarly to detect a signal received from one of the coils or from one of the columns. Thus, while this circuit has the advantage that only 2n wires (plus a ground wire, which is not shown) were required for an $n \times n$ array, as described above, the total number of elements was very substantially limited before the signal-to-noise ratio became so low that it was impossible to determine the location of a defect in the part or, indeed, to determine whether one was present. As also noted above, it would be theoretically possible to connect two individual wires to each of the coils, but for an array with a large number of elements, this would be technologically impractical; for an $n \times n$ array, $n^2 + 1$ connecting wires would be required.

Figure 5:
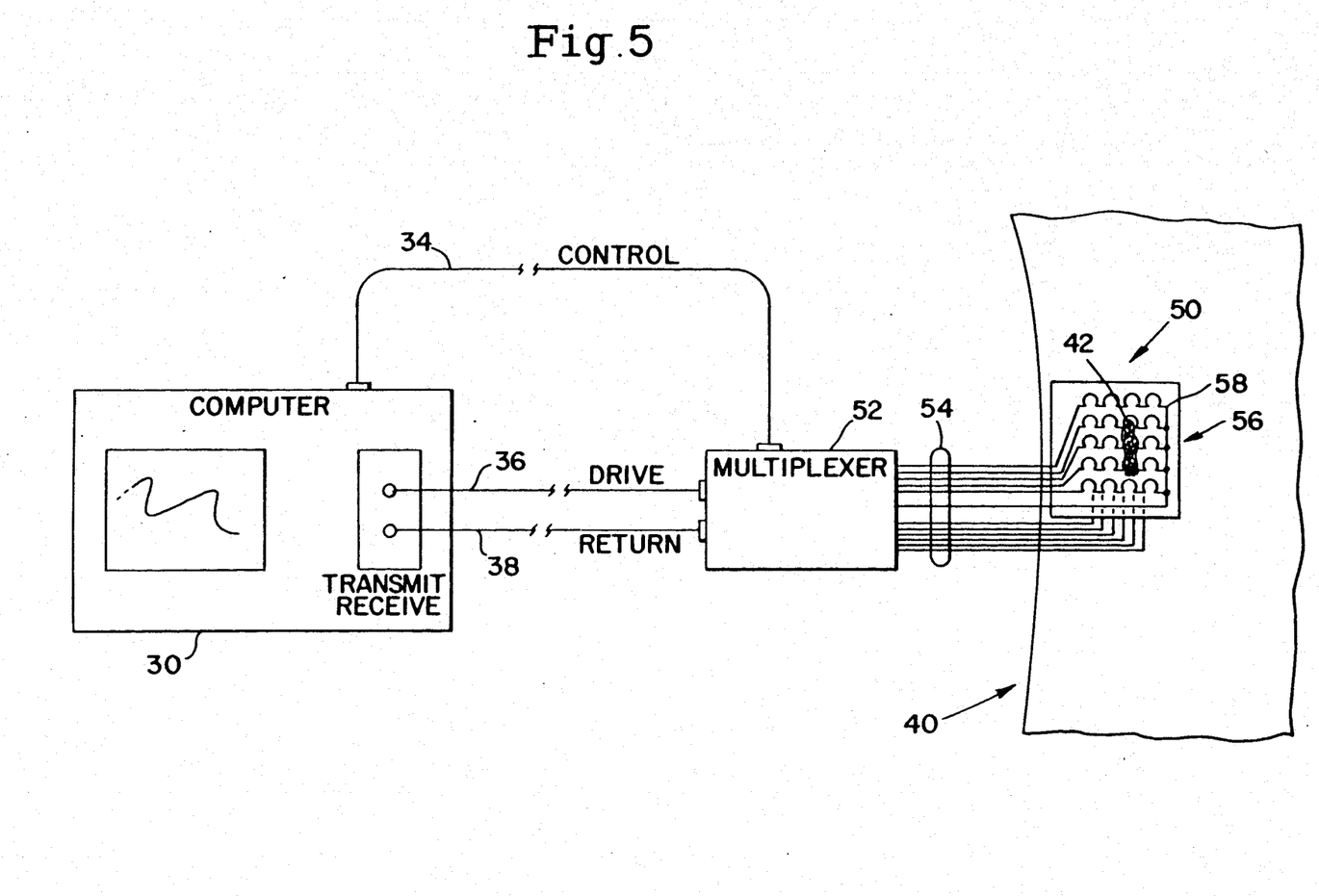
FIG. 5 corresponds to FIG. 1, depicting an eddy-current inspection system according to the present invention.

FIG. 5 is comparable to FIG. 1, and shows the overall inspection system according to the present invention. Again, a computer-based eddy current instrument 30 is connected by control lead 34, drive lead 36 and signal lead 38 to a multiplexer 52 which is connected by a number of wires 54 to the array 50. These elements have the functions discussed above with respect to the prior system of FIG. 1. However, according to the present invention, the driver coils are disposed in columns on one side of a substrate 56, separate detector coils are disposed in rows on the other side of the substrate, and separate conductors 54 are provided between the multiplexer and each of the rows and columns. Thus, while essentially the same number of conductors is provided according to the invention as in the prior device of FIGS. 1-4, the sequence of multiplexing is different, as will be made clear below.

FIGS. 6 and 7 show the detector side and the driver side of the array 50, respectively. These are shown in the same orientation, i.e., as if seen from the same side of the array. In this way, the reader can appreciate that the coils 62 of the driver side (FIG. 7) can be coaxial with the coils 60 of the detector side (FIG. 6) of the array, as is preferable.

Referring now to FIG. 6, the coils 60 of the detector array are organized into a plurality of horizontal rows indicated at 58. The coils are divided into upper and lower half-coils which are in series with one another; these series are connected by the "outermost" coil of each row, while one side of the "inboard" end of each row is connected to a multiplexing switch 66 controlled by multiplexer 52 (FIG. 5), and the other side is a common return line. In a particularly preferred embodiment of the invention, the multiplexing switches 66 can be mounted on the array. In either case, the outputs of the multiplexing switches are connected together at a connection point 68. In this embodiment, multiplexing is accomplished responsive to control signals from the computer 30 (i.e. eliminating the discrete multiplexer 52 of FIG. 5) to activate the corresponding one of the switches 66 to pass signals detected by one or more of the coils 60 of the corresponding row 58. Control signal wires 70 carry an address signal which identifies the particular one of the multiplexing switches to be closed at a particular time. Decoding devices which respond to such control signals are well known, whereby n signal wires are sufficient to control $2^n$ switches.

It would be undesirable to form the control signal wires 20 on the same side of the substrate as the coils, as this would require numerous insulated crossings. Therefore, the detector control wires are formed on the "driver" side of the array, and are connected to the multiplexing switches coil by way of plated through-holes 67, which are well known for making connections between conductors formed on either side of a substrate. The ground lead 65 is similarly connected to one side of each of the rows by through-holes 63. A similar arrangement employing a like number of control leads 84 (FIG. 7) is used to provide control signals to multiplexing switches 82 used to energize the driver coils on the driver side of the array. The common connection to the columns of driven coils is similarly provided, as indicated at 86. The connections are not fully depicted in FIGS. 6 and 7 to avoid overcomplication of the drawings.

FIG. 7 shows a corresponding view of the driver side of the array. Again, a number of coils 72 formed of series-connected pairs of half-coils are organized into a number of columns 74 which are generally orthogonal to the rows 58 of FIG. 6. The outermost coil of each of the columns of coils is complete, connecting the two sets of series-connected half-coils. One side of the other end of each of the columns of coils 72 is connected to a multiplexing switch 82 which controls connection of the corresponding column 74 to a source 78 of excitation energy, which typically is a sinusoid in a frequency range between a few Hertz and about 100 MHz. The other side of each of the columns is common, as shown. One of the columns 74 is selected by supplying a control signal as described above to the multiplexing switches 82 in each column. Those of skill in the art will recognize that a number of additional switching arrangements would be possible.

FIG. 8 shows a circuit diagram of the coil assembly of the invention which is generally comparable to that of FIG. 4. However, unlike the diagram of FIG. 4, the coils of each row n, (each of which comprises two half-coils, as above, in the preferred embodiment), denominated n,1, n,2, ... n,n, of the detector side of the assembly, are electrically isolated from the coils 1,n, 2,n, ... n,n, of each column n of the driver side of the array. Accordingly, only one column of driver coils is energized at any one time, and only the induced voltage detected by one row of detector coils is measured at any one time. The total induced voltage detected by all of the coils in any one row is measured, since the output signals of all the coils of a row are summed. However, in general, the induced voltage measured will be principally due to the contribution from the detector coil directly under the column of driver coils to which the excitation signal is being applied at that time. Therefore, according to the invention, a substantially precise correlation can be made between the row and column being addressed at any given time to a particular portion of the part being inspected. Moreover, the number of coils in both arrays can be multiplied indefinitely without altering this feature.

It will be appreciated that the coils shown in FIGS. 6 and 7 comprise almost complete circles. There are numerous other coil shapes which would also be useful. Spirals could be used as in the prior art coil of FIG. 3; in some applications polygonal or elliptical coils might also be useful. The simple coils shown have the distinct advantage that the conductors need not cross, which greatly simplifies manufacture of the overall assembly. In this connection, it will be appreciated by those of skill in the art that substantially all of the conductors required to be formed on either side of the substrate 56, including the control lines, the power lines, the ground lines, and the coils could all be printed on the substrate in one step. This greatly simplifies manufacture of the array according to the invention.

The use of essentially circular coils as shown also means that the response of the detectors to discontinuities in the member being inspected is radially symmetric, i.e., so that variations in the voltage detected responsive to a discontinuity will be detected equally, regardless of its orientation with respect to the rows of detector coils. This is in distinction to the arrangement of Chamuel, using straight wires; as noted above, to obtain detection of discontinuities in all directions, Chamuel is obliged in his FIG. 7 embodiment to use plural crossed arrays of wires. Even given this arrangement, the signal response would vary depending on the relative orientation of the discontinuity with respect to the wires.

The improved array according to the invention is used by disposing the array in close physical juxtaposition to a member to be inspected, and driving one of the columns of coils with a sinusoid of appropriate frequency while sequentially detecting signals returned from each of the rows. The sinusoid would then be directed to the next column of driver coils, and so on. Alternatively, of course, the signal from one of the rows of detector coils could be monitored continuously while sequentially driving the columns. However, due to the time taken by the driver coils to "settle" after a transient in the driver circuit, the former method is preferred. In either case, if the signal detected from one of the rows changes drastically, this indicates a discontinuity. If the signal detected by all of the rows varies upon power supplied to a particular column, this indicates a discontinuity extending along the column. On the other hand, a variation in the voltage detected with respect to a single row indicates a discontinuity parallel to the row.

It is believed that, given the disclosure of the invention provided above, those of skill in the art will have no difficulty in modifying the prior art driver circuitry, multiplexer and the like shown in FIG. 1 to function properly with an improved array according to the invention. Similarly, fabrication of the array itself is well within the skill of the art, given the above disclosure.

In a preferred embodiment, it is anticipated that the diameter of the coils will be 0.020", that the transverse dimension of the conductors making up the driver coils will be 0.005", and that the copper conductor will have a thickness of 0.001". Use of a polyamide substrate material, such as that sold under the trademark Kapton, in combination with conductors as above, will yield an array sufficiently flexible to be useful in examination of most parts of interest.

It will be apparent to those of skill in the art that while the driver coils have been described as organized into columns and the detector coils organized into rows, these can obviously be reversed. Numerous other arrangements of the invention are also possible. In particular, the row-and-column arrangement shown is highly useful for inspection of rectangularly-shaped members. In some cases, it may be preferable to shape the "array" to fit complexly-shaped parts, such as turbine blades and the like. In these cases, the rows and columns will not necessarily be straight, nor orthogonal to one another. However, addressing of the individual "rows" and "columns" would still be carried out as above, and the coils of the two arrays would still preferably be coaxial. The claims of this application are intended to include such "irregular" shapes where not specifically excluded.

While a preferred embodiment of the invention has been described in detail, those of skill in the art will readily recognize that further improvements and modifications can be made thereto without departure from the spirit and scope of the invention which is, therefore, not to be limited by the above exemplary disclosure, but only by the following claims.

We claim:

1. A flexible coil assembly for non-destructive eddy-current examination of electrically conductive members, comprising:

a flexible planar substrate;

a first array of driver coils disposed on one side of said flexible substrate, said first array comprising a plurality of parallel columns of pairs of coils connected in series to one another, each of said parallel columns of pairs of coils comprising parallel outgoing and return lines, each line consisting of a plurality of series-connected coils, the lines having terminal and opposite ends, the terminal ends of said lines being connected to means for controllably connecting said columns to a source of excitation energy and the opposite ends of said lines being connected to one another, whereby current flows in opposite directions in the outgoing and return lines of each column; and a second array of detector coils disposed on the opposite side of said flexible substrate, said second array comprising a plurality of parallel rows of coils connected in series to one another, said rows extending in a direction other than parallel to said columns, each of said parallel rows of pairs of coils comprising parallel outgoing and return lines, each consisting of a plurality of series-connected coils, the lines having terminal and opposite ends, the terminal ends of said outgoing and return lines being connected to means for controllably connecting said rows to means for processing signals detected by one or more of the coils of the corresponding row, and the opposite ends of said lines being connected to one another, whereby current flows in opposite directions in the outgoing and return lines of each row.

2. The assembly of claim 1, wherein each of the pairs of coils of said rows of detector coils comprises an upper and a lower half-coil, the upper half-coils being connected in series to the lower half-coils.

3. The assembly of claim 1, wherein each of the pairs of coils of said columns of driver coils comprises an upper and a lower half-coil, the upper half-coils being connected in series to the lower half-coils.

4. The assembly of claim 1, further comprising switch means mounted on said substrate for controllably connecting said rows to said means for processing.

5. The assembly of claim 4, wherein said switch means are responsive to control signals provided by control means external to said assembly.

6. The assembly of claim 4, in combination with computer means, and with means for connecting said computer means by a plurality of control lines to said switch means.

7. The assembly of claim 1, further comprising a plurality of controllable switch means mounted on said first substrate, each of said switches being connected to one of said parallel rows of coils, for controlling connection of the corresponding row to a source of excitation energy, and means for supplying control signals to said controllable switch means.

8. The assembly of claim 7, wherein said means for supplying control signals to said controllable switch means is a plurality of control lines connected to control means external to said assembly.

9. The assembly of claim 7, in combination with computer means for providing control signals to said switch means.

10. The assembly of claim 1, wherein said coils and conductors connecting them to form said rows and columns are printed on said flexible substrate.

11. The assembly of claim 10, wherein each of said coils comprises a loop.

12. The assembly of claim 11, wherein said loops are generally circular in outline.

13. The assembly of claim 1, wherein said rows and columns are substantially orthogonal to one another, and said driver coils and detector coils of said arrays are substantially coaxial.

14. A method for non-destructive eddy-current examination of a conductive member, comprising the steps of:

placing an assembly of driver coils and of detector coils in close physical juxtaposition to the member to be examined, said assembly comprising:

a planar substrate;

a first array of driver coils disposed on one side of said substrate, said first array comprising a plurality of parallel columns of coils connected in series to one another, each of said parallel columns of coils comprising parallel outgoing and return conductors, said outgoing and return conductors each being formed to comprise a number of series-connected coils, inner ends of said conductors being connected to means for controllably connecting said columns to a source of excitation energy, and outer ends of said outgoing and return conductors being connected to one another, whereby equal and opposite currents flow in the parallel conductors of each column; and a second array of detector coils disposed on the opposite side of said flexible substrate, said second array comprising a plurality of parallel rows of coils connected in series to one another, said rows extending in a direction other than parallel to said columns, each of said parallel rows of coils comprising parallel outgoing and return conductors, each of said conductors being formed to comprise a number of series-connected coils, inner ends of said conductors being connected to means for controllably connecting said rows to means for processing induced voltage signals detected by one or more of the coils of the corresponding row and outer ends of said conductors being connected to one another, whereby equal and opposite currents flow in the conductors of each column;

sequentially connecting a source of excitation energy to the columns of coils of the first array;

sequentially detecting and measuring the induced voltage signals in the rows of coils of the second array; and analyzing variations in the signals detected by the second array of coils to locate discontinuities in the member to be examined.

15. The method of claim 14 wherein the impedance of each of the rows of coils in the second array is sequentially measured while the source of excitation energy is connected to a single one of the columns of coils.

16. The method of claim 14 wherein said source of excitation energy provides a sinusoidal signal at between 1 Hz and 100 mHz.

17. A system for eddy-current nondestructive examination of conductive members, comprising:

a coil assembly, comprising:

a planar substrate;

a first array of driver coils disposed on one side of said substrate, said first array comprising a plurality of parallel columns of pairs of coils connected in series to one another, the coils of each column being provided as two parallel series-connected arrays, the arrays being connected to one another at a first end of each, and being connected to means for controllably connecting said columns to a source of excitation energy at their second ends; and a second array of detector coils disposed on the opposite side of said substrate, said second array comprising a plurality of parallel rows of coils connected in series to one another, said rows extending in a direction other than parallel to said columns, the coils of each column being provided as two parallel series-connected arrays, the arrays being connected to one another at a first end of each, and being connected to means for controllably connecting said rows to means for processing signals detected by one or more of the coils of the corresponding row;

a source of excitation energy at a predetermined frequency;

first multiplexing means for applying said energy in sequence to the plurality of columns of driver coils comprised by the flexible coil assembly;

second multiplexing means for sequentially receiving and storing induced voltage signals detected by the plurality of rows of detector coils also comprised by said flexible coil assembly; and means for comparing the signals detected by the rows of detector coils and for identifying variations therein, and for determining the row and column of coils with respect to which the signals exhibiting the variations were recorded.

18. The system of claim 17, wherein said second multiplexing means comprises control means providing switch control signals, and switch means, responsive to control signals provided by said control means, mounted on said substrate for multiplexing the induced voltage signals.

19. The system of claim 18, wherein said first multiplexing means comprises a plurality of controllable switch means mounted on said first substrate, each of said switches being connected to one of said parallel rows of coils for controlling connection of the corresponding row to said source of excitation energy, and control line means connected to said control means for supplying control signals to said controllable switch means.

20. The system of claim 17, wherein said coils and conductors connecting them to form said rows and columns are printed on said substrate.

21. The system of claim 20 wherein each of said coils comprises a loop which is not fully closed.

22. The system of claim 21 wherein said loops are generally circular in outline.

23. The system of claim 17 wherein said rows and columns are generally orthogonal to one another and said driver coils and detector coils of said arrays are substantially coaxial.

24. The system of claim 17 wherein said coil assembly is flexible.

25. A flexible coil assembly for non-destructive eddy-current examination of electrically conductive members, comprising:

a flexible planar substrate;

a first array of driver coils disposed on one side of said flexible substrate, said first array comprising a plurality of first groups of coils connected in series to one another, each of said first groups being connected to means for controllably connecting said first groups to a source of excitation energy; and a second array of detector coils disposed on the opposite side of said flexible substrate, said second array comprising a second plurality of second groups of coils connected in series to one another, each of said second groups being connected to means for controllably connecting said second groups to means for processing signals detected by one or more of the coils of the corresponding group wherein each of the coils of said first and second groups of coils comprises a first and a second half-coil, the first half-coils being connected in series to the second half-coils.

26. The assembly of claim 25, further comprising switch means mounted on said substrate for controllably connecting said first and second groups of coils to said source of excitation energy and to said means for processing, respectively.

* * * * *